United States Patent [19]

Janowski

[11] Patent Number: 6,146,620
[45] Date of Patent: Nov. 14, 2000

[54] SHAVING COMPOSITIONS USEFUL IN ALTERING THE GROWTH OF MALE BEARD HAIR

[76] Inventor: Leonard J. Janowski, 1-1 S. Meadow Village, Carver, Mass. 02330

[21] Appl. No.: 08/987,057

[22] Filed: Dec. 9, 1997

[51] Int. Cl.⁷ .................................. A61K 7/06; A61K 7/15
[52] U.S. Cl. ............................ 424/73; 424/401; 514/880; 132/202
[58] Field of Search ..................... 424/73, 401; 132/202; 514/880

[56] References Cited

U.S. PATENT DOCUMENTS

| 4,720,489 | 1/1988 | Shander . |
| 4,885,289 | 12/1989 | Breuer et al. . |
| 5,095,007 | 3/1992 | Ahluwalia . |
| 5,096,911 | 3/1992 | Ahluwalia et al. . |
| 5,271,942 | 12/1993 | Heverhagen . |
| 5,352,437 | 10/1994 | Nakagawa et al. . |
| 5,411,991 | 5/1995 | Shander et al. . |
| 5,674,477 | 10/1997 | Ahluwalia . |
| 5,776,442 | 7/1998 | Ahluwalia . |

*Primary Examiner*—Thurman K. Page
*Assistant Examiner*—Brian K. Seidleck

[57] ABSTRACT

The character of male beard hair growth is altered by employing a conventional shave enhancing composition containing a topically active chemical agent capable of acting upon the sites influencing beard hair growth.

4 Claims, No Drawings

6,146,620

SHAVING COMPOSITIONS USEFUL IN ALTERING THE GROWTH OF MALE BEARD HAIR

This invention relates to a new and novel method and compositions for altering the growth of male beard hair concomitant with the normal daily shaving routine.

BACKGROUND OF THE INVENTION

Many regimens have been used over the years to remove human hair from areas of the skin where it grows from roots located in hair follicles. The most common, approach is shaving the face and neck using a sharpened blade or an electric razor. Alternatives include depilation, electrolysis, epilation, plucking and the topical application of various chemical agents to alter the character of beard hair growth.

Each of these procedures has its own draw backs. Shaving can cause nicks in the skin especially if the individual suffers from acne, pseudo-folliculitis or other condition in which the surface of the skin is not flat. Depilation, while effective, is unsuitable for daily use because of the potential for skin irritation caused by the chemical agents employed in the process. Epilation, involving the application of hot wax or other epilating agents is painful when the hair is stripped away with the solidified epilating agent. Plucking of individual hairs is likewise a painful as well as time consuming process. Electrolysis, generally effective, can be an expensive, time consuming process involving discomfort and the possibility of scarring. The topical application of the various chemical agents described in the prior art to alter beard hair growth require that a composition, suitably formulated for the purpose, be employed in a regimen separate from the daily shaving routine.

U.S. Pat. No. 5,669,916 describes process for inactivating the hair follicle, bringing about the longterm inhibition of hair growth. The process comprises first mechanically or chemically removing the hair from the skin by, for example, hot waxing or the use of a mechanical device to avulse the hair from its follicle. The hair growth-promoting properties of the follicle are then inactivated by any of a plurality of methods including (1) the use of photosensitizers such as porphyrins followed by exposure to light, (2) the application of mild toxins such as peroxides and iodine-releasing agents and (3) the application of electric current.

SUMMARY OF THE INVENTION

I have discovered that male beard hair growth can be reduced gradually without the need for any treatment regimen other than the traditional daily shaving process. This is accomplished by employing, in a novel manner, a shave enhancing composition containing, as an active ingredient, a topically active chemical agent capable of altering the character of beard hair growth. In the practice of the invention, (1) the composition is applied to the skin and beard to prepare it for shaving, (2) the beard hair is removed by shaving in a conventional manner and (3) the residue of the composition is allowed to remain on or rubbed into the skin to bring about delivery of the active material to the sites influencing beard hair growth. The practical result is (1) a gradual reduction in beard cutting forces perceived as improved shaving comfort and (2) reduction of "five o'clock shadow" where the untreated beard is dark or heavy.

DETAILED DESCRIPTION OF THE INVENTION

To make the daily shaving ritual less onerous and to improve the closeness and comfort of the result, a wide range of shave enhancing products have been developed. These products are designed to satisfy two major functional requirements. Firstly, such products must hydrate the beard hair thereby softening it and reducing significantly the force required to cut the hair fibers. Secondly, the product provides lubrication for the passage of the razor over the skin of the face and neck during the shaving process. The better shave enhancing products should also maintain their physical integrity during shaving to provide support to the beard hair, be non-irritating to the skin and non-corrosive with respect to the shaving instrument being used.

Shave enhancing products come in many forms including beard softening creams. When formulated as brushless, non-lathering shaving creams they are typically applied to the wet skin and beard. After a short period of time during which the beard hair becomes hydrated, the beard, along with a portion of the shaving cream is removed from the skin using the razor. Such products often contain soaps, synthetic detergents and materials to improve lubrication, wetting and hydration thus leading to a closer, more comfortable shave. Ingredients such as silicone fluids and mineral oils may also be included to reduce skin friction.

Another popular type of shave enhancing composition is the lather shaving cream which has the ability to supply water to the beard by drainage through the plateau borders formed at the junctions of bubbles in the foam. This type of product is typically a concentrated dispersion of 30–50% alkali metal soaps in water. Up to 15% of a humectant such as glycerol, sobitol or propylene glycol is added to prevent premature drying out of the cream and to make the cream softer.

Probably the most popular form of shave enhancing product is the aerosol shaving foam. These products are typically oil-in-water emulsions in which droplets of a propellant material, liquified under pressure, form a substantial portion of the oil phase. When the container valve is actuated, the product is dispensed as a foam consisting of vaporized propellant droplets surrounded by an aqueous surfactant phase. As in the case of non-aerosol shave enhancing products, described hereinabove, this type of product usually comprises a system including water, one or more soap or synthetic detergent ingredients and ingredients to provide skin lubrication, humectancy, preservation, corrosion inhibition and other desirable attributes.

Another type of aerosol shaving foam product useful in the practice of this invention is the post-foaming aerosol gel. Products of this type are dispensed from aerosol containers as stable gels and spread over the skin and beard where they form a foam in situ by vaporization of low-boiling aliphatic hydrocarbons contained in the formulation.

While the above description of the invention and its practice is couched in the practice of wet shaving in which a sharpened steel razor blade is used to cut softened beard hair fibers at the skin surface, the principles apply equally to the practice of dry shaving in which an electric razor is used to cut the beard hair fibers after they have been raised and stiffened by the application of a suitable shave enhancing composition. This is accomplished by the topical application of a composition formulated to remove the film of perspiration from the skin and to provide a reduction of friction between the shaver head and the skin. The most popular form of pre-electric shave composition comprises an alcoholic solution of a lubricating fatty acid ester such as isopropyl myristate. In adapting pre-electric shave enhancing compositions to the practice of this invention, they are formulated to include a topically active chemical agent capable of altering the character of beard hair growth as described hereinafter.

The technology of formulating shave enhancing compositions of the above and other types is described in detail in the prior art and is readily available to those wishing to prepare such products. In addition to the many relevant prior art patents, formulation principles and examples may be found in various compendia such as Harry's Cosmeticology (7th edition, 1989) pages 156–159.

The compositions useful in the practice of this invention comprise the combination of a conventional shave enhancing composition and a topically active chemical agent capable of altering the character of beard hair growth by reducing the rate of growth, reverting growth to the vellus form or largely eliminating further growth thereby reducing the hair cutting forces encountered in the shaving operation.

A number of such agents are described in the patent art among them:

U.S. Pat. No. 4,720,489—ornithine decarboxylase inhibitors, 5-alpha-reductase inhibitors and cytoplasmic androgen receptor binding agents;

U.S. Pat. No. 4,885,289—5-alpha-reductase inhibitors and cytoplasmic androgen receptor binding agents;

U.S. Pat. No. 5,095,007—Inhibitors of adenylsuccinate synthetase and aspartate transcarbamylase;

U.S. Pat. No. 5,096,911—Inhibitors of gammaglutamyl transpeptidase;

U.S. Pat. No. 5,271,942—Aqueous solutions of urea;

U.S. Pat. No. 5,411,991—Non-depilatory compositions containing sulfhydryl active compounds and U.S. Pat. No. 5,674,477—Catechin compounds derived from green tea leaves.

As can readily be seen, a wide variety of chemical species is represented in the above compilation. In formulating hair growth altering agents in the shave enhancing compositions useful in the practice of this invention, reference should be made to the prior art describing such agents for specific formulation requirements or limitations. The effective amount of hair growth altering agent which may be used covers a wide range and varies from agent to agent. In general, from about 0.1 to about 20.0 per cent by weight or more where solubility permits, may be employed to provide hair growth modification capabilities to the compositions useful in the practice of this invention. While the optimum amounts will vary from agent to agent and from individual to individual, good results can be obtained by employing from about 0.5 to about 10.0 per cent by weight. Assuming a single daily application as part of the shaving regimen, measureable growth changes will occur within several days to as long as several weeks depending on which agent is employed, the amount in the formulation and response rate of the individual. The effectiveness of the compositions may be enhanced by the inclusion of ingredients known to aid the absorption of active materials into the skin such as lanolin derivatives and benzyl alcohol.

As mentioned hereinabove, the topically active chemical agent capable of altering the character of beard hair growth is included as an ingredient in a conventional shave enhancing composition, several types of which have already been described. The composition is used in the daily shaving ritual as normally practiced except that the residual composition remaining after shaving is not rinsed from the skin but is, instead, allowed to remain on or rubbed into the skin to bring about delivery of the active material to the sites influencing beard hair growth. If desired, a small additional amount of the composition may be applied to the skin after shaving to increase the amount of the active material available for delivery. The cosmetic effects of use of these products are optimized when they are formulated taking into account the principles and ingredients known to be useful in the formulation of cosmetic skin creams.

The following examples are illustrative of the compositions and method to be used in the practice of this invention but should not be construed as limiting.

EXAMPLE 1
BEARD SOFTENING SHAVING CREAM

| Ingredient | Weight % |
| --- | --- |
| oleic acid | 5.4 |
| coconut oil fatty acids | 4.4 |
| alkyl aryl polyethylene glycol ether | 2.0 |
| propylene glycol | 5.5 |
| monoethanolamine | 1.3 |
| triethanolamine | 2.8 |
| mixture of catechin compounds derived from green tea leaves | 10.0 |
| water | q.s. to 100.0 |

Procedure: After combining the fatty acids and stirring into the propylene glycol, the amines are added and the mixture stirred to yield a clear solution. The alkyl aryl polyethylene glycol ether and mixture of catechin compounds are then added followed by the water.

The product is applied to the pre-wetted beard and allowed to remain for 1–2 minutes before shaving to further hydrate the beard hair fibers. After the beard has been removed by shaving, the shaving cream remaining on the face and neck is rubbed lightly into the skin. After several days of such use measurable growth changes will occur.

EXAMPLE 2
AEROSOL SHAVING FOAM

| Ingredient | Weight % |
| --- | --- |
| palmitic acid | 4.5 |
| lauric acid | 1.5 |
| polyacrylic acid (40% aq.) m.w. 100,000 | 1.5 |
| polyethylene glycol (400) monolaurate | 0.5 |
| sodium lauryl sulfate | 1.2 |
| triethanolamine | 2.0 |
| potassium hydroxide | 0.8 |
| glycerol | 4.9 |
| N-acetyl-L-cysteine | 10.0 |
| water | q.s. to 100.0 |

Procedure: The mixture of fatty acids is heated to about 75° C. and combined, with vigorous stirring, with a mixture of the other ingredients which has been heated to the same temperature. After cooling to room temperature, 97.0 parts of the composition and 3.0 parts of a propellant mixture are loaded into a conventional aerosol container sealed with a valved actuator.

The product is expelled from the container as a foam and applied to the pre-wetted beard and allowed to remain for 1–2 minutes to further hydrate the beard hair fibers. After the beard has been removed by shaving the remaining shaving cream is rubbed lightly into the skin. After several days of such use measurable growth changes will occur.

EXAMPLE 3
POST FOAMING AEROSOL GEL

| Ingredient | Weight % |
| --- | --- |
| stearic acid | 2.0 |
| palmitic acid | 5.8 |
| polyoxyethylene (2) cetyl ether | 1.0 |
| hydroxyalkyl cellulose | 0.1 |
| carboxypolymethylene | 0.2 |
| propylene glycol dipelargonate | 2.8 |
| sorbitol (70% solution) | 10.0 |
| propylene glycol | 3.3 |
| triethanolamine | 4.2 |
| cyproterone acetate | 6.0 |
| water | q.s. to 100.0 |
| n-butane | 0.6 |
| n-pentane | 2.1 |

Procedure: A soap intermediate is first prepared by adding an aqueous solution of sorbitol and triethanolamine to the fatty acids and polyoxyethylene (2) cetyl ether at 80° C. Separate solutions of the hydroxyalkyl cellulose in aqeuous propylene glycol and carboxypolymethylene in water are added to the soap intermediate at 27° C. A mixture of the hydrocarbons and remaining ingredients and an equal volume of propylene glycol at 4° C. is mixed with the remainder of the formulation in a manner to avoid trapping air in the gel. The gel is immediately transferred to the inner compartment of a barrier aerosol dispenser and the valve crimped in place. The outer compartment is pressurized with about 10 ml. of a mixture of propane and isobutane providing a pressure of about 46 psi at 25° C.

The product is expelled from the container as a stable gel which is spread on the beard to form a layer of foam by virtue of the vaporization of the low-boiling aliphatic hydrocarbons. After a 1–2 minute wait to allow the beard hair fibers to become hydrated, the beard is removed by shaving. The remaining shaving foam is rubbed lightly into the skin. After several days of such use measurable growth changes will occur.

It will be appreciated by those skilled in the art that the invention can be practiced within a wide range of parameters of method, composition or conditions without departing from the spirit or scope of the invention.

I claim:

1. A method of shaving beard hair comprising applying to the beard hair a conventional shave enhancing composition selected from the class consisting of beard softening creams, lather shaving creams, aerosol shaving foams, post foaming aerosol gels and pre-electric shaving compostions, said shave enhancing composition being combined with an effective amount of a topically active chemical agent capable of reducing the rate of beard hair growth, removing said beard hair by shaving and rubbing the residue of said shave enhancing composition into the skin or allowing it to remain on the skin to bring about delivery of said topically active agent to sites influencing beard hair growth.

2. The method of claim 1 in which the concentration of topically active chemical agent is between about 0.1 to about 20.0 per cent by weight.

3. The method of claim 1 in which the concentration of topically active chemical agent is between about 0.5 to about 10.0 per cent by weight.

4. The method of claim 1 in which the topically active chemical agent is selected from the class consisting of ornithine decarboxylase inhibitors, 5-alpha-reductase inhibitors, cytoplasmic androgen receptor binding agents, inhibitors of adenylsuccinate synthetase, inhibitors of aspartate transcarbamylase, inhibitors of gammaglutamyl transpeptidase, aqueous solutions of urea, sulfhydryl active compounds and catechin compounds.

* * * * *